(12) United States Patent
Mak

(10) Patent No.: US 9,487,458 B2
(45) Date of Patent: Nov. 8, 2016

(54) CONFIGURATIONS AND METHODS FOR NITROGEN REJECTION, LNG AND NGL PRODUCTION FROM HIGH NITROGEN FEED GASES

(71) Applicant: FLUOR TECHNOLOGIES CORPORATION, Aliso Viejo, CA (US)

(72) Inventor: John Mak, Santa Ana, CA (US)

(73) Assignee: Fluor Corporation, Sugar Land, TX (US)

( * ) Notice: Subject to any disclaimer, the term of this patent is extended or adjusted under 35 U.S.C. 154(b) by 297 days.

(21) Appl. No.: 14/194,238

(22) Filed: Feb. 28, 2014

(65) Prior Publication Data

US 2015/0246859 A1 Sep. 3, 2015

(51) Int. Cl.
*C07C 7/09* (2006.01)
*C10G 5/06* (2006.01)

(52) U.S. Cl.
CPC .. *C07C 7/09* (2013.01); *C10G 5/06* (2013.01)

(58) Field of Classification Search
None
See application file for complete search history.

(56) References Cited

U.S. PATENT DOCUMENTS

| 3,596,472 | A | * | 8/1971 | Streich | F25J 1/0022 62/623 |
| 4,451,275 | A | | 5/1984 | Vines | |
| 4,662,919 | A | | 5/1987 | Davis | |
| 5,141,544 | A | | 8/1992 | Butts | |
| 5,341,646 | A | * | 8/1994 | Agrawal | F25J 3/0409 62/646 |
| 5,375,422 | A | | 12/1994 | Butts | |
| 8,453,403 | B2 | | 6/2013 | Wheeler | |
| 8,627,681 | B2 | | 1/2014 | Malsam | |
| 2007/0157663 | A1 | * | 7/2007 | Mak | F25J 1/0022 62/620 |
| 2010/0051876 | A1 | * | 3/2010 | Filippi | C01B 3/025 252/377 |
| 2010/0223950 | A1 | * | 9/2010 | Malsam | C10L 3/10 62/611 |
| 2011/0239701 | A1 | | 10/2011 | Kaart | |
| 2012/0036890 | A1 | | 2/2012 | Kimble | |
| 2012/0167617 | A1 | | 7/2012 | Anghel | |

FOREIGN PATENT DOCUMENTS

WO 2010060735 A2 6/2010
WO 2012177405 A1 12/2012

* cited by examiner

*Primary Examiner* — Tam M Nguyen
(74) *Attorney, Agent, or Firm* — Conley Rose, P.C.; Kristin Jordan Harkins

(57) ABSTRACT

Variable N2 content in feed gas ranging from 3 mole % to 50 mole % can be rejected from the process using a feed exchanger that is fluidly coupled with a cold separator and a single fractionation column to produce a nitrogen vent stream and streams that are suitable to be further processed for NGL recovery and LNG production.

14 Claims, 2 Drawing Sheets

CONFIGURATIONS AND METHODS FOR NITROGEN REJECTION, LNG AND NGL PRODUCTION FROM HIGH NITROGEN FEED GASES

FIELD OF THE INVENTION

The field of the invention is gas processing high nitrogen feed gas for separating nitrogen from methane and other hydrocarbon components from natural gas streams for the production of LNG and NGL.

BACKGROUND OF THE INVENTION

The following description includes information that may be useful in understanding the present invention. It is not an admission that any of the information provided herein is prior art or relevant to the presently claimed invention, or that any publication specifically or implicitly referenced is prior art. Moreover, all publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Because of the relatively high value of gas condensate and liquids, oil gas fields are often injected with nitrogen to enhance production, leading to a substantial increase in nitrogen content in the fields over time. Most typically, the initial nitrogen content in the fields is low, at about 1 to 3 mol %, but as the fields mature, and with continuous nitrogen injection, the nitrogen content can increase to as high as 15 to 30 mol %. Such high nitrogen content requires in most cases the use of a nitrogen rejection unit (NRU) to meet pipeline gas inert specification that are generally at less than 2 mol % for nitrogen.

Variable and high nitrogen content is also problematic where gas is stored underground in gas storage facilities, particularly during withdrawal and injection cycles. When gas demand is low during summer, excess gas must be injected to the gas storage reservoirs, and when demand is high during winter, gas is withdrawn from the reservoirs. During the withdrawal cycle, it has been observed that the nitrogen content of the withdrawn gas varies from 3 mol % to as high as 30 mol %. To address this problem, most operators install a nitrogen rejection unit to produce on-spec pipeline gas.

Most NRUs operate at cryogenic temperature, as low as −300° F., and for this reason, water and $CO_2$ content must be reduced to ppm levels (e.g., 1 ppmv water, 50 ppmv $CO_2$) to so avoid freezing of water and $CO_2$ in the cryogenic section. Additionally, if the natural feed gas contains significant amounts of aromatics, wax formation and associated operating difficulties will arise, which is a well-known problem in LNG liquefaction plants.

Moreover, the nitrogen content for LNG liquefaction must be kept very low, typically at levels of less than 1 mol % as high nitrogen content in LNG increases refrigeration horsepower demand and hence the liquefaction cost. In addition, high nitrogen LNG has higher boiloff rates during storage and transport, resulting in higher product losses. For these reasons, excessive nitrogen should be removed prior to liquefaction to improve LNG economy. Additionally, heavy hydrocarbons in LNG should be removed to meet the Methane Number specification for vehicles (Methane Number is typically 80 or higher), to minimize emissions from higher hydrocarbons.

One method of removing nitrogen from a natural gas stream is processing of the gas in a NRU, and typical configurations comprising two cryogenic columns are described in U.S. Pat. Nos. 8,435,403 and 4,451,275. Two column systems are particularly advantageous when the feed gas contains large amounts of nitrogen, and where the gas is relatively rich (i.e., has substantial content of higher hydrocarbons). The first column generally operates as a pre-fractionation column operating at high pressure, which removes the heavy hydrocarbon as a bottom liquid, while generating a methane and nitrogen overhead that is fractionated in the second column at a lower pressure. Typically, nitrogen content greater than 15% is deemed suitable as feed gas for plants with two column design. However, two column systems are rarely used for lower nitrogen content (3% or less) and would require in most cases nitrogen recycle to avoid excessive methane losses in the nitrogen vent, which in turn, increases the capital and operating cost of the plant.

On the other hand, an NRU may also be configured to operate with a single fractionating column, and exemplary single column systems are described in U.S. Pat. Nos. 5,141,544, and 5,375,422. Single column systems can advantageously operate at low nitrogen content (e.g., as low as 3 mol %) without nitrogen recycle. They are also often less capital intensive due to the lack of a second column, but require substantially more power to operate on high nitrogen gases. Still further, single column systems are typically limited to processing lean gases, and without use of a pre-fractionation column, heavy hydrocarbons will build up in the system. Therefore, external refrigeration may be required. Additionally, most single column systems use an integral reflux condenser, which is limited to low nitrogen content gases with low reflux requirements.

Compounding difficulties in the operation of NRUs is the fact that most known NRU processes fail to operate efficiently on feed gases with a wide range of nitrogen content (e.g., 3 mol % to 50 mol %) and variable hydrocarbon content. Moreover, many of the known NRU processes require additional refrigeration, heat exchangers, and columns in addition to the basic single or two-column configuration.

Thus, although various NRU configurations and methods are known in the art, all or almost all of them suffer from one or more disadvantages, especially where the feed gas has variable nitrogen content over a relatively wide range and further comprises relatively large quantities of heavier hydrocarbons (e.g., $C3^+$). Therefore, there is still a need to provide improved methods and configurations for nitrogen removal.

SUMMARY OF THE INVENTION

The inventive subject matter is directed to various systems, methods, and configurations for nitrogen removal from a hydrocarbonaceous feed gas that allows for removal of variable quantities of nitrogen and recovery of $C3^+$ components in a conceptually simple and elegant manner.

In one aspect of the inventive subject matter, the inventor contemplates a method of removing nitrogen from a hydrocarbonaceous feed gas that has a CO2 content of equal or less than 50 ppmv, a water content of equal or less than 0.1 ppmv, and a nitrogen content of at least 3 mol %. Preferred methods include a step of cooling the hydrocarbonaceous feed gas in a heat exchanger to condense $C3^+$ components in the hydrocarbonaceous feed gas, and a further step of separating the condensed $C3^+$ components in a phase separator as a liquid stream from a vapor stream that predominantly comprises C1, C2, and nitrogen. The vapor stream is then fed into a refluxed fractionation column that produces a nitrogen-enriched overhead product and a nitrogen-depleted bottom product. The nitrogen-enriched overhead product is partially condensed using refrigeration generated by pressure reduction of one portion of the nitrogen-depleted bottom product to so produce a liquid reflux to the fractionation column and a gaseous nitrogen vent stream. The liquid reflux is fed to the fractionation column, while the gaseous nitrogen vent stream is vented to the atmosphere and/or flare.

In especially contemplated configurations and methods, the hydrocarbonaceous feed gas has a pressure of about 800-1000 psia, and the hydrocarbonaceous feed gas is cooled to a temperature of −40° F. to −60° F., and it is further contemplated that at least 80% of the $C3^+$ components are condensed upon cooling the hydrocarbonaceous feed gas. With respect to the condensed $C3^+$ components it is generally contemplated that refrigeration content is used in a heat exchanger and that the so heated $C3^+$ components are then fed to a NGL recovery unit that produces a $C3^+$ NGL product and a vapor product (which may be fed to a LNG liquefaction unit). With respect to the vapor stream it is typically preferred that the vapor steam is at least partially condensed before it is fed into the fractionation column.

Where desired, the gaseous nitrogen vent stream may be reduced in pressure and refrigeration content may be extracted in the heat exchanger and/or reflux exchanger. Likewise, the pressure reduced portion of the nitrogen-depleted bottom product may be used to cool other process streams (preferably in the heat exchanger) and may be recompressed and fed to the LNG liquefaction unit. Similarly, another portion of the nitrogen-depleted bottom product may be used to provide refrigeration content in the heat exchanger, and the so heated portion may be fed to a LNG liquefaction unit.

Consequently, the inventor also contemplates a method of removing nitrogen from a hydrocarbonaceous feed gas (e.g., at a pressure of at least 700 psia) having a CO2 content of equal or less than 50 ppmv, a water content of equal or less than 0.1 ppmv, and a nitrogen content of at least 3 mol %. In preferred methods, the hydrocarbonaceous feed gas is cooled to form a liquid stream comprising condensed $C3^+$ components and a vapor stream comprising C1, C2, and nitrogen. The vapor stream is then separated in a refluxed fractionation column (e.g., operated at a pressure of 300-400 psia) into a nitrogen-enriched overhead product and a nitrogen-depleted bottom product, and the pressure of the nitrogen-depleted bottom product is reduced to produce refrigeration for cooling the feed gas and to provide the majority of the refrigeration requirement for the reflux condenser. The so cooled nitrogen-enriched overhead product is then separated into a gaseous nitrogen vent stream and a reflux stream.

In preferred methods, the pressure-reduced nitrogen-depleted bottom product is fed to a natural gas liquefaction unit, and/or the liquid stream is heated (in the heat exchanger) and fed to a natural gas liquids recovery unit to form a $C3^+$ NGL product and a vapor product, which may also be fed to the natural gas liquefaction unit.

Therefore, and viewed from a different perspective, the inventor also contemplates a plant with a nitrogen removal unit and a natural gas liquids recovery unit. Particularly preferred plants include or are coupled to a feed gas source that provides a hydrocarbonaceous feed gas with a CO2 content of equal or less than 50 ppmv, a water content of equal or less than 0.1 ppmv, and a nitrogen content of at least 3 mol %. As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

A heat exchanger then receives and cools the hydrocarbonaceous feed gas to a temperature that condenses C3+ components in the hydrocarbonaceous feed gas, while a phase separator receives the cooled hydrocarbonaceous feed and separates the condensed C3+ components as a liquid stream from a vapor stream that comprises C1, C2, and nitrogen. Most typically, the liquid stream is then transported via a conduit from the phase separator to a natural gas liquids recovery unit. A refluxed fractionation column receives the vapor stream and produces a nitrogen-enriched overhead product and a nitrogen-depleted bottom product, wherein a reflux condenser partially condenses the nitrogen-enriched overhead product using refrigeration of a pressure-reduced first portion of the nitrogen-depleted bottom product to so produce a liquid reflux to the fractionation column and a gaseous nitrogen vent stream. As noted above, a natural gas liquefaction unit is fluidly coupled to the refluxed fractionation column and receives the first portion of the nitrogen-depleted bottom product and a second portion of the nitrogen-depleted bottom product.

In further contemplated aspects, the heat exchanger receives and cools the vapor stream to at least partially condense the vapor stream prior to entry into the fractionation column, heats the gaseous nitrogen vent stream, and/or receives and heats the second portion of the nitrogen-depleted bottom product. Where desired, a compressor is included that re-compressed the second portion of the nitrogen-depleted bottom product. It is further generally contemplated that the natural gas liquids recovery unit produces a vapor product that is fed to the natural gas liquefaction unit via a conduit.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
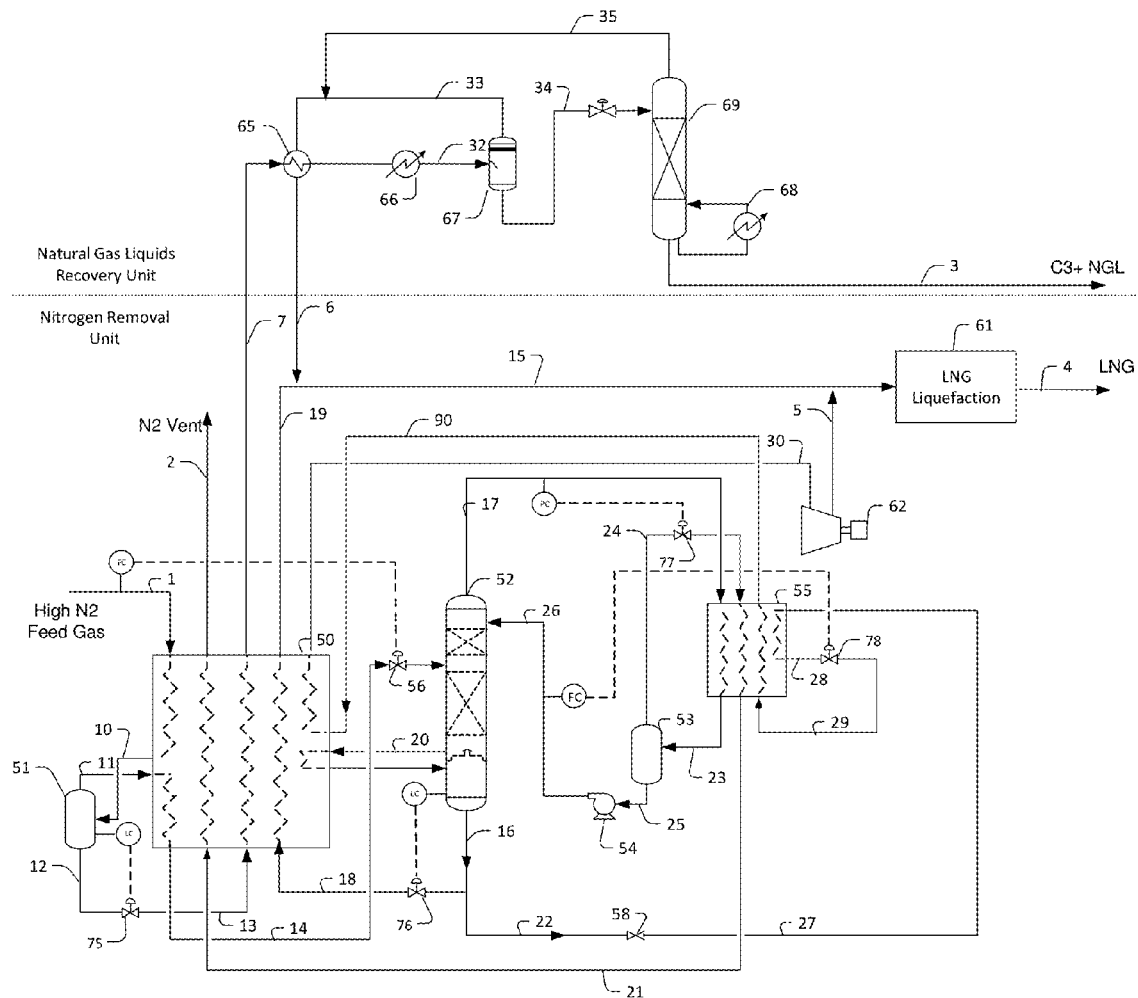
FIG. 1 depicts an exemplary configuration of a nitrogen rejection system that produces LNG and NGL.

The inventor has discovered that hydrocarbonaceous feed gases with variable content of nitrogen can be effectively processed to remove nitrogen to acceptable levels while producing a natural gas product (predominantly comprising methane and to a lesser extent ethane) that can be readily liquefied, as well as a natural gas liquids fraction that can be processed in an NGL unit to produce a $C3^+$ product. Notably, all or almost all of the refrigeration requirements are satisfied by expansion cooling of various process streams, and especially of the fractionation column bottom product and a liquid stream that comprises condensed $C3^+$ components.

Viewed from a different perspective, the inventor also contemplates various systems and methods that allow for efficient nitrogen removal using a single column that is configured to produce streams suitable for NGL recovery and LNG production. Especially preferred systems and methods are particularly suitable for NRU feed gas flow rates ranging from 50 MMSCFD to 300 MMSCFD. Most typically, the feed gas is pretreated in one or more upstream units to a residual water content of about 0.1 ppmv and a residual CO2 content of about 50 ppmv. In still further contemplated systems and methods, the feed gas composition may vary considerably, and suitable feed gases include relatively rich feed gases (e.g., over 5 mol % C3+ components) with variable nitrogen content (e.g., 3 mol % to 50 mol %). As used herein, and in conjunction with a numeral, the term "about" refers to a range of +/−10% of that numeral, endpoints inclusive. The recitation of ranges of values herein is merely intended to serve as a shorthand method of referring individually to each separate value falling within the range, including endpoints. Unless otherwise indicated herein, each individual value with a range is incorporated into the specification as if it were individually recited herein.

In one aspect of the inventive subject matter, contemplated systems and methods employ a single column that is fluidly coupled with a cold separator that is configured and operated such as to allow for removal of the majority (e.g., at least 50%, more typically at least 70%, most typically at least 80%) of the $C3^+$ contents in the feed gas prior to entering the column. Thus, in most cases, the cold separator is a simple phase separator (as opposed to an absorber or a column with trays or packing or other separation devices) that operates at relatively low temperatures. Still further, it should be appreciated that the cold separator will also typically operate at a pressure that is equal to or about the feed gas pressure (e.g., at least 700, psia, more typically at least 800 psia, even more typically at least 900 psia, and most typically between 900-1500 psia and in some cases even higher).

For example, suitable operating temperatures for contemplated cold separators will typically be in the range of about −40° F. to −60° F. at a pressure of at least 800 psia (or other pressure as noted above), which will remove at least 80% of the $C3^+$ components contained in the feed gas. It should be appreciated that such conditions are advantageous for at least two reasons: First, such low temperatures will effectively condense most of the heavier components in the feed gas at a pressure that is about the same as the feed gas pressure. Second, and after removal of the $C3^+$ components as a liquid fraction, the liquid fraction can be further cooled by pressure reduction to a pressure level at which a downstream NGL operates (e.g., about 300-600 psia) to so provide refrigeration content to the process (most typically to the feed exchanger). The liquid fraction will have a temperature of between about −20° F. to 40° F. prior to processing in the downstream NGL recovery unit, thus allowing the $C3^+$ components to bypass the NRU column and processing of the liquid fraction in the NGL recovery unit. Most typically, residual methane is separated from the liquid fraction in an upstream phase separator and/or in a stabilizer as described in more detail below.

Therefore, it should be appreciated that contemplated systems and methods will also include an NGL recovery unit that will fractionate the $C3^+$ components from the cold separator liquid, and that the NGL recovery unit is independently operable from the NRU. Most typically, independent operation is achieved by condensation of the heavy components from the feed gas such that variable heavy components in the feed gas can be separated out without affecting the processing rate of the lighter components (e.g., C1/C2, nitrogen, and various inert compounds). Preferably a level control unit in the cold separator will assist in setting the appropriate flow rate of the liquid to the NGL recovery unit. Viewed from another perspective, it should be appreciated that inclusion of an NGL recovery unit with the NRU is particularly desirable as the feed liquid to the NGL recovery unit contains concentrated $C3^+$ components with low nitrogen content, regardless of the nitrogen content in the feed gas. Moreover, as a consequence of using the heated liquid fraction (via feed exchanger) from the cold separator, it should be noted that the NGL recovery unit can be operated at temperature above −20 to −40° F., allowing for use of carbon steel material in the NGL recovery unit, which substantially reduces material costs as compared to heretofore known integrated processes.

Thus, collocation of the LNG liquefaction unit and the NRU are especially preferred. In still further contemplated aspects, at least some of the process streams of the NRU could also be thermally integrated with the liquefaction unit. For example, where residual refrigeration content is available from a process stream in the NRU, cooling requirements could be reduced for the liquefaction process. On the other hand, where residual refrigeration content is available from a process or product stream of the liquefaction unit, refrigeration requirements of the NRU could be supplemented with such content.

In most contemplated methods and configurations, the feed gas is chilled and condensed at relatively high pressure (typically about 800 psig or above) using refrigeration content from various internally generated cold streams, the nitrogen vent gas, and/or the column reboiler. In further preferred aspects, it should be appreciated that the vapor fraction is once more subjected to further cooling in the feed cooler, and the so condensed stream is then reduced in pressure via a JT valve (or other expansion/pressure reduction device) and fed into the fractionation column operating at about 300 to 350 psig (or higher pressure). It should be particularly appreciated that the column produces an overhead nitrogen stream containing about or less than 1 mol % methane and a bottom hydrocarbon stream containing about or less than 1 mol % nitrogen. The so formed liquid bottom stream containing the desired natural gas is then split into two portions with both portions being used to provide refrigeration content to the processing scheme. More specifically, one portion (25 to 50%) is used to supply the predominant share of the refrigeration duty of the reflux exchanger, while the other portion is used to supply at least some of the refrigeration duty in the feed exchanger.

In still further preferred aspects of the inventive subject matter, all process streams of the NRU and NGL recovery unit are collected such that all value products can be recovered at on-spec quality while only venting nitrogen with minimal (about 1 mol % or less) hydrocarbon loss. Most preferably, all non-$C3^+$ streams originating in the NGL recovery unit will be recycled to the natural gas product (e.g., for liquefaction), and it should be recognized that such recycling need not be routed through the NRU as the liquid fraction from the cold separator has already a very low nitrogen content. Therefore, the feed gas to the LNG liquefaction plant typically includes residue gas from the NGL recovery unit and a low pressure effluent stream from the NRU (after having provided refrigeration content). These streams are lean (with minimal C3+ content) and are suitable to meet the Methane Number requirements of the LNG product. It should further be appreciated by those skilled in the art that references to separation of nitrogen and methane used herein refer to processing NRU feed gas to produce various multi-component product streams containing large amounts of the particular desired components (e.g., typically at least 90%, more typically at least 95%, most typically at least 97%), but not pure streams (i.e., at least 99.99% or higher) of any particular component. For example, one of the product streams is a nitrogen vent stream, which is primarily comprised of nitrogen but may have relatively small amounts of other components, such as methane and ethane (e.g., 1-2 mol %). Another product stream is an NGL product stream, which is primarily comprised of propane and butane (e.g., collectively at least 97 mol %), but may contain some amounts of other components, such as hexane and pentane. A third product stream, according to another embodiment of the invention, is the LNG product stream, which is primarily methane and ethane (e.g., collectively at least 97 mol %).

One exemplary configuration and method is shown in FIG. 1, where feed gas entering the plant has been pretreated for CO2 and water removal. In most cases, the CO2 content is at or below 150 ppmv, more typically at or below 100 ppmv, and most typically at or below 50 ppmv. CO2 removal can be performed in all known manners, and particularly suitable CO2 removal methods include physical and/or chemical absorption processes, membrane separation, and sublimation. Similarly, the water content is generally at or below 1 ppmv, more typically at or below 0.5 ppmv, and most typically at or below 0.1 ppmv to avoid freezing problems in the downstream equipment. There are numerous water removal systems and methods known in the art (e.g., glycol dehydration, molecular sieve dehydration, etc.), and all of those are deemed suitable for use herein.

Feed gas stream 1 enters the NRU at a feed rate of 100 MMscfd at a pressure of about 940 psia and a temperature of about 95° F. The nitrogen content in the feed gas ranges from 3 mol % to 50 mol %, or higher. The feed gas flow rate is controlled by JT valve 56 just before the column. The feed gas is cooled to about −40° F. to −60° F. in exchanger 50 forming stream 10 which is separated in cold separator 51, producing vapor stream 11 and liquid stream 12. The liquid stream containing at least 60%, more typically at least 70%, and most typically at least 80% of the $C_3^+$ components is letdown in pressure via JT valve 75, forming stream 13 and heated in exchanger 50 providing the refrigeration duty for feed chilling while the vapor stream 11 from the cold separator is chilled and condensed in exchanger 50 at s temperature of about −150° F. to about −180° F. forming cold condensate stream 14. It should be noted that the amount of cooling and the particular operating temperatures will at least in part depend on the nitrogen and hydrocarbon content of the feed gas. The cold condensate 14 is letdown in pressure using JT valve 56 to about 360 psia to feed fractionation column 52.

Liquid stream 13 is heated in feed exchanger 50 forming stream 7 that is used to feed the NGL recovery unit which typically includes an exchanger 65, refrigerant chiller 66 (forming chilled stream 32) and phase separator 67 (as opposed to an absorber or a column with trays or packing or other separation devices). Phase separator vapor stream 33 is combined with stabilizer overhead 35 and the combined streams are heated in exchanger 65, forming stream 6 to feed the LNG liquefaction unit 61 that produces LNG product 4. Separator liquid stream 34 is routed to stabilizer 69 that fractionates the liquid into $C_3^+$ NGL stream 3 and overhead vapor stream 35. In most cases, over 90% of the $C_3^+$ content can be recovered as a bottom liquid from the stabilizer that is typically reboiled with reboiler 68.

In the NRU unit, the fractionation column 52 fractionates the cold feed stream 14 into a nitrogen rich overhead stream 17 and a methane rich bottom stream 16, using reflux condenser 55 for rectification and reboiler stream 20 for stripping. Nitrogen rich overhead stream 17 with typically at least 90%, more typically at least 95%, and most typically at least 98% nitrogen (e.g., 99%) content is cooled and partially condensed in reflux condenser 55 forming two-phase stream 23 which is separated in separator 53 into nitrogen vapor stream 24 and hydrocarbon liquid stream 25. The liquid stream 25 is pumped by reflux pump 54 forming reflux stream 26, wherein the flow rate is controlled by the coolant provided using JT valve 78. Nitrogen stream 24 is letdown to close to atmospheric pressure via JT valve 77, providing a portion of the reflux condenser cooling duty before providing as stream 21 further cooling in exchanger 50. Heated stream 21 leaves the plant as nitrogen vent stream 2.

Figure 2:
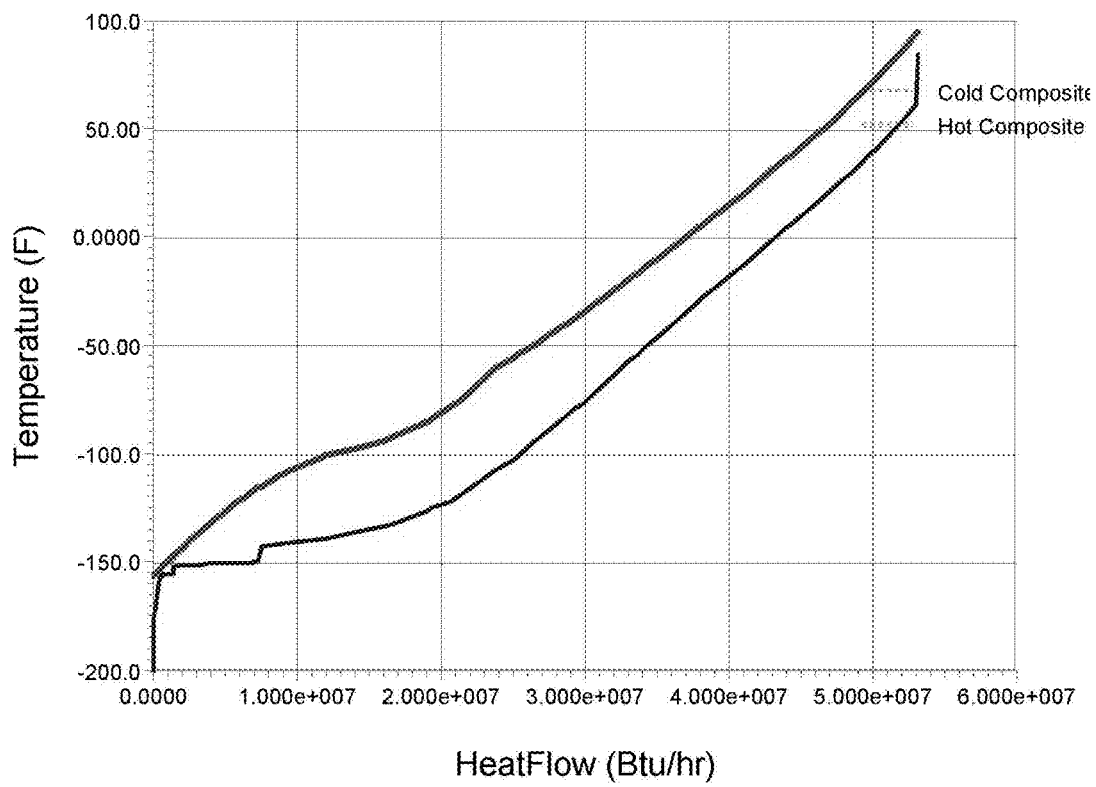
FIG. 2 depicts a composite curve of the feed exchanger of the exemplary system of FIG. 1.

The methane rich bottom stream 16 is split into two portions. One portion, stream 22, is routed via valve 58 as stream 27 to reflux condenser 55 and cooled to about −242° F., forming stream 28 which is letdown in pressure in JT valve 78 forming stream 29, providing a majority (at least 50%, more typically at least 70%, most typically at least 85%) of the cooling duty of the reflux condenser. Exchanger outlet stream 90 is heated in exchanger 50, forming stream 30 which is compressed to about 300 psia by compressor 62, forming a compressed stream 5 for combination with stream 15 to LNG liquefaction unit 61. The feed exchange heat composite curve is shown in FIG. 2, demonstrating the close temperature approach and high efficiency of the process.

The remaining portion 18 of the methane rich bottom stream 16, under level control by valve 76, is used for feed gas cooling in exchanger 50. The so heated exit gas vapor stream 19 forms a third stream to the LNG plant 61. Exit gas stream 19 is typically combined with stream 6 from the NGL recovery unit (forming stream 15) and compressed stream 5. The overall mass balance of the contemplated plant is shown in Table 1 below.

TABLE 1

| Stream | Feed Gas (1) | N2 Vent (2) | C3 + NGL (3) | LNG (4) |
| --- | --- | --- | --- | --- |
| CO2 | 0.00 | 0.00 | 0.00 | 0.00 |
| N2 | 2.88 | 99.25 | 0.00 | 0.78 |
| C1 | 85.38 | 0.75 | 0.00 | 91.13 |
| C2 | 3.19 | 0.00 | 1.00 | 3.36 |
| C3 | 4.25 | 0.00 | 31.65 | 3.13 |
| iC4 | 3.11 | 0.00 | 43.62 | 1.38 |
| nC4 | 0.50 | 0.00 | 8.18 | 0.17 |
| iC5 | 0.16 | 0.00 | 3.39 | 0.02 |
| nC5 | 0.13 | 0.00 | 2.90 | 0.01 |
| Pressure, psia | 840 | 15 | 99 | 15 |
| Temperature, ° F. | 95 | 84 | 100 | −262 |
| Flow MMscfd | 99.8 | 2.2 | 4.2 | 93.5 |

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of removing nitrogen from a hydrocarbonaceous feed gas having a CO2 content of equal or less than 50 ppmv, a water content of equal or less than 0.1 ppmv, and a nitrogen content of at least 3 mol %, comprising:
    cooling the hydrocarbonaceous feed gas in a heat exchanger to condense $C3^+$ components in the hydrocarbonaceous feed gas;
    separating in a phase separator the condensed $C3^+$ components as a liquid stream from a vapor stream comprising C1, C2, and nitrogen;
    feeding the vapor stream into a fractionation column, and using the fractionation column to produce a nitrogen-enriched overhead product and a nitrogen-depleted bottom product;
    partially condensing the nitrogen-enriched overhead product using refrigeration generated by pressure reduction of a portion of the nitrogen-depleted bottom product to thereby produce a liquid reflux to the fractionation column and a gaseous nitrogen vent stream; and
    feeding the liquid reflux to the fractionation column.

2. The method of claim 1 wherein the hydrocarbonaceous feed gas has a pressure of about 800-1000 psia, and wherein the hydrocarbonaceous feed gas is cooled to a temperature of −40° F.' to −60° F.

3. The method of claim 1 wherein at least 80% of the $C3^+$ components are condensed in the step of cooling the hydrocarbonaceous feed gas.

4. The method of claim 1 further comprising a step of heating the condensed $C3^+$ components and feeding the heated $C3^+$ components to a natural gas liquids recovery unit that is configured to produce a $C3^+$ NGL product and a vapor product.

5. The method of claim 4 further comprising a step of feeding the vapor product to a natural gas liquefaction unit.

6. The method of claim 1 further comprising a step of at least partially condensing the vapor stream before feeding the vapor stream into the fractionation column.

7. The method of claim 1 further comprising a step of reducing pressure of the gaseous nitrogen vent stream and extracting refrigeration content from the gaseous nitrogen vent stream in at least one of the heat exchanger and a reflux exchanger.

8. The method of claim 1 further comprising a step of compressing the pressure reduced portion of the nitrogen-depleted bottom product and feeding the recompressed portion of the bottom product to a natural gas liquefaction unit.

9. The method of claim 1 further comprising a step of heating another portion of the nitrogen-depleted bottom product in the heat exchanger, and feeding the heated another portion to a natural gas liquefaction unit.

10. A method of removing nitrogen from a hydrocarbonaceous feed gas having a CO2 content of equal or less than 50 ppmv, a water content of equal or less than 0.1 ppmv, and a nitrogen content of at least 3 mol %, comprising:
    cooling the hydrocarbonaceous feed gas to form a liquid stream comprising condensed $C3^+$ components and a vapor stream comprising C1, C2, and nitrogen;
    separating in a refluxed fractionation column the vapor stream into a nitrogen-enriched overhead product and a nitrogen-depleted bottom product;
    reducing pressure of the nitrogen-depleted bottom product to produce refrigeration for the step of cooling the feed gas and refrigeration for a reflux condenser to so form from the nitrogen-enriched overhead product a gaseous nitrogen vent stream and a reflux stream.

11. The method of claim 10 further comprising a step of feeding the pressure-reduced nitrogen-depleted bottom product to a natural gas liquefaction unit.

12. The method of claim 10 further comprising a step of heating the liquid stream and feeding the heated liquid stream to a natural gas liquids recovery unit to form a $C3^+$ NGL product and a vapor product.

13. The method of claim 12 wherein the vapor product is fed to a natural gas liquefaction unit.

14. The method of claim 10 wherein the hydrocarbonaceous feed gas has a pressure of at least 700 psia, and wherein the refluxed fractionation column is operated at a pressure of 300-400 psia.

* * * * *